(12) United States Patent
Fishman et al.

(10) Patent No.: US 7,147,865 B2
(45) Date of Patent: *Dec. 12, 2006

(54) ARTIFICIAL SYNAPSE CHIP

(75) Inventors: Harvey A. Fishman, Menlo Park, CA (US); David Bloom, Jackson, WY (US); Stacey F. Bent, Palo Alto, CA (US); Mark C. Peterman, Jackson, WY (US); Jaan Noolandi, Palo Alto, CA (US); Neville Mehenti, East Windsor, NJ (US)

(73) Assignee: The Board of Trustees of the Leland Stanford University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/713,565

(22) Filed: Nov. 13, 2003

(65) Prior Publication Data

US 2004/0224002 A1 Nov. 11, 2004

Related U.S. Application Data

(63) Continuation-in-part of application No. 10/184,210, filed on Jun. 27, 2002, now Pat. No. 7,001,608.

(60) Provisional application No. 60/450,980, filed on Feb. 27, 2003, provisional application No. 60/301,934, filed on Jun. 29, 2001.

(51) Int. Cl.
*A61F 2/14* (2006.01)

(52) U.S. Cl. .......................... 424/427; 424/422; 623/4.1; 623/6.63; 623/24; 623/25; 623/26; 435/395; 435/325

(58) Field of Classification Search ................ 623/4.1, 623/6.63, 24, 25, 26; 435/325, 375, 366, 435/395; 606/152
See application file for complete search history.

(56) References Cited

U.S. PATENT DOCUMENTS

| 4,474,751 | A | | 10/1984 | Haslam et al. ................ 424/78 |
|---|---|---|---|---|
| 5,962,027 | A | | 10/1999 | Hughes |
| 6,045,791 | A | | 4/2000 | Liu |
| 6,071,597 | A | * | 6/2000 | Yang et al. .................. 428/209 |
| 6,668,190 | B1 | * | 12/2003 | Iezzi et al. .................... 604/20 |
| 6,676,675 | B1 | * | 1/2004 | Mallapragada et al. ..... 606/152 |
| 6,692,481 | B1 | | 2/2004 | Guerrero .................... 604/521 |

(Continued)

FOREIGN PATENT DOCUMENTS

WO    WO 98/22819    5/1998

(Continued)

OTHER PUBLICATIONS

Fishman et al, ARVO Annual Meeting Abstract Search and Program Planner, Abstract No. 2846, vol. 2002, Annual Meeting of the Association For Research in Vision and Opthalmology. Fort Lauderdale, FL, May 5-10, 2002.*

(Continued)

*Primary Examiner*—Leon B. Lankford, Jr.
*Assistant Examiner*—Allison M. Ford
(74) *Attorney, Agent, or Firm*—Lumen Intellectual Property Services, Inc.

(57) ABSTRACT

Devices and methods are provided for administering a fluid to a neuronal site. The device comprises a reservoir, an aperture in fluid connection to the reservoir, and electrical means for moving to the fluid to or through the aperture. The electrical means may take the form of electroosmotic force, piezoelectric movement of a diaphragm or electrolysis of a solution. The electrical means may be external to the host, implanted in the host or may be photodiodes activated by light, particularly where the neuronal site is associated with the retina.

22 Claims, 8 Drawing Sheets

U.S. PATENT DOCUMENTS

2002/0087202 A1    7/2002  Chow et al. .................. 607/53

FOREIGN PATENT DOCUMENTS

WO    WO 01/81552    11/2001
WO    WO 03/002190 A2    1/2003

OTHER PUBLICATIONS

Peterman et al., "Localized Neurotransmitter Release for Use in Prototype Retinal Interface," 2003 IOVS 44, 3144.

Maghreibi et al., "Stretchable Micro-Electrode Array," Poster 149, 2nd Annual International IBEE-EMBS Special Topic Conference on Microtechnologies in Medicine and Biology, May 2-4, 2002, Madison, WI.

L. Lu et al., "Retinal pigment epithelium cell culture on this biodegradable poly(DL-lactic-co-glycolic acid) films", J. Biomater Science Edn. vol. 9, No. 11, pp. 1187-1205 (1998).

T. Dintelmann et al., "Comparative study of ROS degradation by IPE and RPE cells in vitro", Graefe's Arch Clin. Excp. Ophthalmology 1999, No. 237, pp. 830-839.

C.D. James et al., "Aligned Microcontact Printing of Micrometer-Scale Poly-L-Lysine Structures for Controlled Growth of cultured Neurons on Planar Microelectrode Arrays", IEEE Transaction On Biomedical Engineering, vol. 47, No. 1, Jan. 2000, pp. 17-21.

U. Hartmann et al., "Human and porcine anterioe lens capsule as support for growing and grafting retinal pigment epithelium and iris pigment epithelium," Graefe's Arch Clin Exp Opthalmology (1999), vol. 237, pp. 940-945.

G. Thumann et al., Transplantation of Autologous Iris Pigment Epithelium After Removal of Choroidal Neovascular Membranes, Arch Opthalomology (Oct. 2000), vol. 118, pp. 1350-1355.

L. Lu et al., "Retinal pigment epithelial cell function on substrates with chemically micropatterned surfaces", Biomaterails ( Dec. 1999), vol. 20, No. 23/24, pp. 2351-2361.

Lappas et al., "Clinical investigation: Iris pigment epithelial cell translocation in exudative age-related mascular degeneration, A pilot study in patents", Graefe's Archive for clinical Experimental Ophthalmology, Abstract, vol. 238 issue, pp. 1 and 2 electronic version, ISSN: 1435-702X.

Giordano et al., "Retinal pigment epithelium cells cultured on synthetic biodegradable polymers", (Abstract) http://www.ncbi.nlm.nih.gov/entres/query.fcgi?cmd=Retrieve&db=PubMed&List_uids=897...6.

T. Abe et al., "Auto iris pigment epithelial cell transplantation in patients with age-related macular degeneration: short-term results", (Abstract) http://www.n.../query.fcgi?cmd=Retrieve&dblist=PubMed&List_uids=10896035&dopt=Ab.

T. Abe et al., "Functional analysis after auto iris pigment epithelial cell transplantation in patients with age-related macular degeneration", (Abstract) http://www.n.../query.fcgi?cmd=Retrieve&db=PubMed&List_uids=10739164&dopt=Abst.

J. Nicolini et al., "The anterior lens capsule used as support material in RPE cell-transplantation", (Abstract) http://www.ncbi.nlm.gov/entrez/query.fcgi?cmd=Retrieve&db=PubMed&List_uids=11C...7.

Sandyk, R. "Paroxysmal Itching in Multiple Sclerosis During Treatment with External Magnetic Fields" (1994) Published in Int. J. Neurosci. 75(1-2): 65-71.

Heuschkel, M.O. et al. Buried Microchannels in Photopolymer for Delivering of Solutions to Neurons in a Network. (1998) Published in Sensors and Actuators B 48: 356-361.

Yeung, C.K. et al. "Modulation of the Growth and Guidance of Rat Brain Stem Neurons Using Patterned Extracellular Matrix Proteins." (2001) Published in Neuroscience Letters 301: 147-150.

Maher, Michael et al. "The Neurochip: A New Multielectrode Device for Stimulating and Recording from Cultured Neurons" (1999) Published in Journal of Neuroscience Methods 87: 45-56.

Jenkner, Martin et al. "Interfacing a Silicon Chip to Pairs of Smail Neurons Connected by Electrical Synapses" (2001) Published in Biol. Cybern 84: 239-249.

Saneinejad, Samar et al. "Patterned Glass Surface Direct Cell Adhesion and Process Outgrowth of Primary Neurons of the Central Nervous System" (1998) Published in J. Biomed. Mater. Res. 42: 13-19.

Tai, Hsin-Chien et al. "Neurite Outgrowth and Growth Cone Morphology on Micropatterned Surfaces" (1998) Published in Biotechnol. Prog. 14: 364-370.

Litke, A.M. "The Retinal Readout System: A Status Report" (1999) Nuclear Instruments and Methods in Physics Research A 435: 242-249.

Bernard, Andre et al. "Printing Patterns of Proteins" (1998) Published in Langmuir vol. 14: 1-5.

Chow, Alan. "Implantation of Silicon Chip Microphotodiode Arrays into the Cat Subretinal Space." (2001) Published in IEEE vol. 9: 86-95.

Mayne, A.H. "Biologically Interfaced Porous Silicon Devices" (2000) Published in Phys. Stat. Sol. 182: 505-513.

Fishman, H.A. "The Artificial Synapse Chip: A Novel Interface for a Retinal Prosthesis Based on Neurotransmitter Stimulation and Nerve Regeneration" (2002) Published in ARVO.

\* cited by examiner

ARTIFICIAL SYNAPSE CHIP

CROSS-REFERENCE TO RELATED APPLICATIONS

This application is a continuation-in-part of Ser. No. 10/184,210, filed Jun. 27, 2002 now U.S. Pat. No. 7,001,608, which claimed priority of provisional application Ser. No. 60/301,934, filed Jun. 29, 2001, and provisional application Ser. No. 60/450,980, filed Feb. 27, 2003, which are incorporated herein in their entirety as if set forth herein.

BACKGROUND OF THE INVENTION

1. Field of the Invention

The field of this invention is microfabricated medical devices.

2. Background Information

Light entering the eye through the cornea is focused through the lens (which further focuses the light) onto the retina, a thin layer of cells in the back of the eye. Normal human vision depends upon signals generated by neurons in the retina. The visual signals originate with the photoreceptor cells in the retina, which sense and respond to light, generating signals that in turn create and shape nerve signals in retinal ganglion cells. Neurons often have extended cellular portions called cell processes, which may be specialized for receiving information and stimulation or for transmitting information. For example, the specialized elongated processes that conduct neuronal impulses are termed axons. The axons of the retinal ganglion cells carry the visual signals from the retina to the brain. In the brain, neuronal networks process the visual experience of a normally-sighted person. The point at which neurons communicate with each other is called a synapse. The average neuron forms about 1000 synaptic connections and may receive up to 10,000 connections. Disturbances at any step in the process may lead to visual impairment or blindness.

Age-related macular degeneration (AMD) is one of the most common forms of blindness in people over the age of 65. Currently, there is no effective treatment for most patients with AMD, a disease that often results in permanent damage to photoreceptors, but spares most retinal ganglion cells (RGCs) and second-order neurons, such as bipolar and horizontal cells. Similarly, other diseases such as retinitis pigmentosa (RP) cause visual impairment and blindness due to loss of photoreceptors.

Inherent to the power of the human visual system is the ability to transduce light by individual photoreceptors, thus making it a high-resolution image capture system. Several groups worldwide have carried out clinical experiments to determine if stimulating retinal cells, the optic nerve bundle or cells of the visual cortex with microelectrode arrays can generate phosphenes (i.e. sensations of light) in individuals impaired with AMD. The electrical fields produced by the microelectrode arrays stimulate relatively large regions containing numerous neuronal and glial cells. These trials have shown that by stimulating neurons with a microelectrode array, blind individuals can indeed recognize a simple pattern such as a horizontal or vertical line. Although these trials have demonstrated that vision is recoverable in a limited fashion, major challenges remain. Due to the size and difficulties in placement of most available electrodes, imprecise electric field stimulation extending over long distances (several cell-body diameters) is used to depolarize neurons. However, such methods often require excessive stimulation, which may be harmful, leading to inflammation of the stimulated region and even to excessive growth of glial cells or gliosis.

The limitations in using electrical stimulation warrant the need for other methodologies that do not use electrical stimulation. The natural method of stimulation employs biologically active molecules that at very low concentrations become bound to neuronal receptors resulting in transduced signals, a process known as synaptic transmission. The neurons respond by changing their polarization and producing electrical signals that are transmitted to other neurons. There is an interest in providing devices that would controllably release biologically active compounds in a restricted space to stimulate one or a few neurons as required to provide a signal.

In diseases where some of the neurons have become incapacitated, such as in macular degeneration, there are still many neurons that are still viable and active, but lack connections to other neurons for receiving signals. By artificially stimulating such viable neurons, there is the opportunity to provide responses to visual signals, so that the brain can interpret the signals and provide a visual output of the signals, giving the experience of seeing. Desirably, one would wish to be able to activate specific neurons in response to visual cues, so that a more accurate pattern of signals is sent to the brain for interpretation.

While the great advancements over the past few years in microfabrication have opened up many opportunities for high-resolution interfaces to the nervous system, the properties of the materials typically used in microfabrication contrast strongly with the natural tissues of the body. The microfabricated materials, often crystalline or ceramic in composition, are solid and "hard," whereas most biological tissues are flexible and "soft."

For biocompatibility, it would be preferable that one should choose techniques and materials that better mimic the native system to achieve better adaptability and success with an implant. One particular organ that has a substantial need for treatment is the eye, where the retina is subject to, for example, macular degeneration and submacular choroidal neovascularization. By using materials that conform to the shape of the retina and fold to simplify implantation, a device is less likely to cause damage during implantation and less likely to cause long-term damage while implanted. For subretinal implants, the device should be thin and small to allow for implantation and reattachment of the retina.

Alternative methods and devices are needed that will allow for controlled stimulation of neurons in a precise way. By allowing for control of one or a few neurons in relation to an external stimulus one can more closely mimic the natural way neuronal cells are stimulated and transmit signals to the brain to permit a visual image or other information.

RELEVANT LITERATURE

Peterman et al., Localized Neurotransmitter Release for Use in Prototype Retinal Inerface 2003 IOVS 44, 3144. See also, Maghreibi, et al., Stretchable Micro-Electrode Array, Poster 149, 2nd Annual International IBEE-EMBS Special Topic Conference on Microtechnologies in Medicine and Biology, May 2–4, 2002, Madison, Wis. U.S. Patent Application Nos. 2002/0087202 and 2002/01882882 and WO03/002190A2. and references cited therein.

SUMMARY OF THE INVENTION

Prostheses are provided for controlled release of neurologically active compounds. A neural interface is provided where one: brings a nerve and stimulation source together; and/or stimulates the nerve cell. For directing the nerve process to a desired site for stimulation, chemical guidance techniques, such as micropatterned surfaces, and/or physical patterning techniques, microfabricated polymer scaffolds, are employed to guide the process in three dimensions. The process is guided to the prostheses where the process can be specifically stimulated. The prosthesis can then serve as an artificial synapse chip (ASC).

The ASC comprises a microfabricated aperture (a "nanoaperture") that provides for controlled release of a biologically active agent. In a preferred embodiment, the ASC is comprised of a flexible film. The film comprises at least one reservoir, each reservoir connected to the nanoaperture for release of the active agent into the surrounding space. Electrodes are provided for flow regulation of the fluid content of the device. The electrodes may be layered on the film and connected to the flow regulator for directing the active agent to or through the aperture to the treatment site. The small prosthesis can be readily introduced in proximity to neurons, e.g. retinal neurons, while providing for a controlled electrical source, either internal or external to the host, for releasing controlled amounts of the reservoir contents to a neuronal site. The devices can be prepared using silicon or silicon compounds. Alternatively, the devices can be prepared from biocompatible prepolymers that are polymerized on a form to provide a film with a cavity that is then covered with an adhesive layer to close the cavity and form a reservoir with the aperture as its outlet. Either or both of the layers may be coated with electrically conducting material to provide electrodes for controlling the flow of the reservoir contents. For the eye, the implant device can be inserted at a retinal site.

DETAILED DESCRIPTION OF THE INVENTION

Figure 1A:
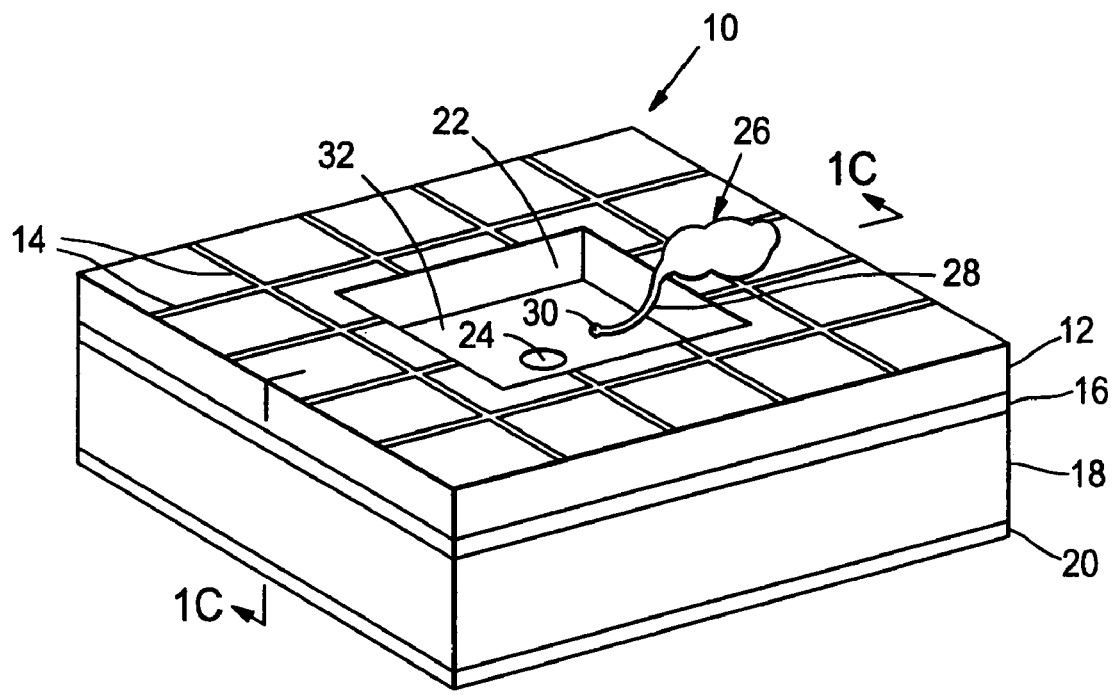
FIG. 1A shows a perspective view of an artificial synapse chip embodying features of the invention.

Microfabricated biocompatible prostheses or implant devices are provided for: directing neuronal processes to a site for neuronal activity modulation; and/or releasing controlled amounts of a therapeutic fluid to a neuronal area to modulate the neuronal activity. The devices are small for ease of implanting and maintenance at the implant site. By providing for patterning on the surface of the device, neuronal processes are directed to an aperture in the device. The device independent of the process growth to the aperture can serve as a controlled source of a biologically active agent as part of the process growth and direction or independent of such growth and direction. The device is also referred to as an artificial synapse chip (ASC).

Device

Housing

The devices comprise a housing, generally in the form of a thin film, usually formed from two layers, that comprise a reservoir, an aperture in fluid connection with the reservoir and a flow regulator. Devices can be produced that have a single unit or multiple units, where the multiple units may be divided into individual or a smaller number of units. Electrodes that may be formed on one or both of the layers provide an electric field for transferring the channel contents to or through the aperture to the site of treatment. The contents of at least one reservoir will usually include a fluid that is biologically active or a solution having a biologically active solute (referred to as a bioactive agent or a bioagent) and with multiple reservoirs, one or more reservoirs may have buffer solution. The flow regulator may employ, for example, electroosmotic force, a piezoelectric driven diaphragm, piston, movable diaphragm, e.g. electrolysis of a salt solution in a sealed container, etc. A source of electricity is connected to the electrodes to control the release of the device contents into the area surrounding the aperture, where the source of electricity may be external or internal. For flow regulation by electroosmotic force, the fluid will include ions for carrying the current.

The housing may be rigid or flexible. Rigid devices may be prepared from silicon, silicon nitride, or polymers that are listed below, where rigidity or flexibility relies on the average molecular weight, degree of cross-linking, and the degree of physical interaction between strands, e.g. hydrogen bonding, entwining, etc.

Dimensions

The devices may be prepared as individual units, that comprise a reservoir, optionally a channel, and aperture, or as multiple units and then divided into individual or smaller multiple units or retained as large multiple units. The individual unit will generally have a surface area in the range of about 2 to $50\mu^2$, more usually about 5 to 25 $\mu^2$, where larger or smaller surface areas may be employed in particular environments. For the retinal use, the surface area will usually not exceed $15\mu^2$, more usually not exceed $10\mu^2$ and will generally have a surface area of at least about $2\mu^2$. Multiple units will generally have a surface area in the range of about 10 to $500\mu^2$, more usually not more than about $200\mu^2$. Apertures will generally be spaced apart at least about $2\mu$, more usually at least about $5\mu$ and generally not more than about $50\mu$, more usually not more than about $25\mu$. The larger the area, the more desirable to have the device shaped to accommodate the particular surface to provide the desired interaction and to localize the agent that is expressed from the device. The devices may have a generally round, elliptical, rectangular, tubular or other form, where the edges may be rounded.

The layers that form the device will generally have a thickness in the range of at least about 20μ and not more than about 2 mm, usually not more than about 0.5 mm, where when an adhesive layer is used, it will have a thickness in the lower part of the range. The layer thickness provides mechanical stability and ease of handling of the device in implanting the device, particularly for implanting in the epiretinal or subretinal region, and ease of retrieving the device when the contents are spent or the device is no longer required.

The implant will be shaped to fit in the region in which it is to be placed. For example, for the retina, the device must be small enough to fit comfortably against the retina in the retinal region, epiretinal or subretinal. While larger and smaller devices may be constructed, generally the thickness of the device will be in the range of about 20–500μ, more usually from about 50 to 300μ.

Housing Composition

The housing is composed of a biologically compatible, and non-biodegradable material, desirably flexible. For rigid materials, silicon or silicon nitride can be employed. For materials that may be flexible or rigid, depending upon the molecular weight and degree of crosslinking, one may employ organic polymers, such as polysiloxanes (e.g. poly (dimethylsiloxane {PDMS})), polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, cellulose acetates, polymethyl methacrylates, ethylene vinyl acetates, polysulfones, nitrocelluloses and mixtures, derivatives and copolymers thereof. In a preferred embodiment, the housing is composed of polysiloxanes. The housing may be transparent or semi-opaque or opaque.

In order to have EOF pumping, it is necessary that the walls be charged. Charging of the walls can be achieved in a variety of ways, such as charged monomers that are copolymerized with the primary prepolymer, modification of the prepolymer to introduce random or regularly spaced charged groups, modifying the surface by oxidation using high energy radiation, etc. In addition, the surface may be coated with charged materials, such as proteins. These ways are well established in the art and do not require exemplification here. Alternatively, additives in the medium can be used to provide the charged surface. While the surface of both layers may be charged with the same charge, only the lower layer comprising most of the channel surface need be charged.

Various groups can provide negative or positive charges. Carboxyl, phosphate, phenol, borate, silicic acid, etc. can provide negative charges. Amine, amidine, hydrazine, etc. can provide positive charges. Oxidation of the surface can lead to carboxyl groups or hydroxyl groups that may also play the role of providing a negative charge.

Typically, the desired polymer is one with a low glass transition temperature, $T_g$. The lower the glass transition temperature the higher the flexibility. The glass transition temperature for poly(dimethylsiloxane) is typically in the order of 146° K. Polymers may be functionally modified by changing the structure to increase or decrease their "softness". For instance, combining two polysiloxane chains into a ladder structure, insertion of rigid groups into the structure, or adding bulky side groups will all increase rigidness. The housing may be further modified to present a zeta potential at the fluid interface, which is advantageous when the flow regulation means is electroosmotic. In another example, poly(dimethylsiloxane) may be functionally modified by plasma irradiation, which oxidizes the methyl groups present, liberating the carbon atoms and leaving hydroxyl groups in their place. This modification effectively creates a glass-like surface on the polymeric material, with its associated hydroxyl functional groups.

Outer Surface

The outer surface of the device may include a well surrounding the aperture. The well will generally have a depth of about 0.1 to 25, usually 0.5 to 20μ and a volume of about 100 pL to 10 μl. Alternatively, there need be no well but a smooth surface.

A micropattern may be provided on the device outer surface proximal to a neuronal site comprising a viable neuron(s). The micropattern provides for directing the growth of a cell process (a neurite with a growth cone). The micropattern directs the neurite to the device aperture for treatment with the biologically active agent(s) dispensed by the device.

Conveniently, the micropattern can be produced using a microcontact printing stamp having an ordered assemblage of molecules, which may be a discontinuous assemblage, for deposition on to a substrate. Microfabrication methods are suitable for making microcontact stamps. The microcontact stamp can be used for deposition of material onto the surface of an ACS. Micropatterns formed by such microcontact printing methods are effective to align the position and growth of cells on a substrate. Stamps may be made of any convenient material, e.g. poly(dimethylsiloxane). The pattern selected will be determined by the interaction with the neuronal process(es) and the pattern of distribution of the neuronal process(es) on the surface of the device.

Microstamps may be fabricated using photolithography techniques. A stamp may be formed from a thin (1–7μ) photoresist layer on a silicon wafer that is patterned to create a master for the microcontact printing. The master pattern consists of arrays of lines configured for cell attachment and neuron growth. The master can be prepared by ultraviolet etching of a mask on a positive photoresist on silicon and PDMS stamps generated in situ on the master using, for example, Sylgard 184 silicone elastomer followed by thermal curing. Stamps can also be prepared by pouring an elastomer and curing agent together to form PDMS on a silicon master, degassed and allowed to set at room temperature. The stamps are then made by cutting a portion of the PDMS followed by plasma treatment to increase hydrophobicity for enhanced protein adsorption and may be imaged using SEM. The patterned layer may be attached to a support layer of the device or may serve to enclose a second layer comprising the features of the flow system of the device.

The substrate for the micropattern may be glass, silicon, silicon nitride, polyimide, polystyrene, polyethylene, polylactide, Teflon®, polysiloxane, or other substrate suitable for cell growth, either directly or with a cell compatible coating, e.g. protein.

A variety of different stamp patterns may be produced by the methods and adapted to the optimal line width or thickness, length and spacing for neurite growth. For example, line widths ranging from a few nanometers wide to several hundreds of micrometers wide may be used; preferably, line widths range from about 10 nm to about 20μ. Lines may be as short as a few nm and may be as long as several millimeters; preferably line length is within the range of about 10 nm to about 100μ long. The spacing between lines in a pattern may range from about 1μ to about 500μ; preferably line spacing is between about 2μ to about 100μ.

Following microfabrication of the microstamp, the stamp is coated with agents to direct the growth of the neurite and other agents that may serve additional purposes. The agents may include various neurotrophins, growth factors, basement membrane components, co-stimulatory agents, antibodies, adhesion agents, etc. Adhesion agents include poly (L-lysine), cell Tak™, neural cell adhesion molecule (N-CAM), etc. During development of the device, the adhesion agent may be labeled with a fluorescent label for visualization. Cell adhesion and growth may then be monitored with a fluorescence microscope. A mercury arc lamp may be used to excite the fluorescent dye to provide a fluorescence signal for visualization of the labeled adhesion agent, whereby the neuronal process can be detected.

Various factors that are known to aid in the growth and direction of neurites can be included in the patterning to direct the neurite to a desired site, e.g. aperture. Factors that may be included are nerve growth factor, brain-derived growth factor (BDGF), epidermal growth factor (EGF), ciliary neurotrophic factor (CNTF), glial-derived neurotrophic factor (GDNF), NT-3, acidic or basic fibroblast growth factor (a- or bFGF), insulin-like growth factor (IGF), platelet derived growth factor (PDGF), vascular endothelial growth factors (VEGF), and others; cyclic nucleotides, such as cAMP, cGMP, etc.; extracellular matrix molecules, such as laminin, tenascin, collagen, fibronectin, integrins, immunoglobulins, cell adhesion molecules, such as N-CAM and L-CAM, axonin, cadherins, etc., proteoglycans, anosmin-1, thrombospondin, myelin and myelin associated inhibitors, such as myelin-associated glycoprotein and nogo; tyrosine kinase receptors, such as ephrins; netrins; inflammatory cytokines, such as TGF-β, leukemia inhibitory factor (LIF), tumor necrosis factors (TNF), interleukins; neurotransmitters, such as acetylcholine, GABA, glutamate, glycine, etc.; stimulatory molecules, such as potassium salts, insulin; as well as any other factors that will aid in the growth, direction and maintenance of the neuron and its processes.

Microconduits

In conjunction with the device, a conduit unit may be used for directing neuronal processes. Microconduits or channels at least approximately orthogonal, usually at an angle of not less than 60° to the surface may be employed to direct processes above the device toward the device, particularly the aperture (s). For each aperture, there may be one or a plurality of such channels, where the opening of the channels may be directly above the aperture or displaced not more than about 2 mm from the aperture. The channels may be defined by pipes, tubes or screen having openings in the range of about 0.1 to 5μ in diameter, where a plurality of channels will generally be separated by walls of about 0.005 to 0.5 mm thick. The height of the channels will generally be at least about 0.05 mm and not more than about 1 mm, generally not more than about 0.5 mm. The same materials used for construction of the housing may be used for construction of the conduit unit. These channels serve to physically confine the neurite growth. The conduit unit can be easily constructed using polymer microfabrication methods and may be constructed as part of the housing or bonded to the housing or other technique for holding the conduit unit in juxtaposition to the housing.

Reservoir

The reservoir contains the bioactive agent or buffer for delivery and has access to the aperture directly or via a channel. Each reservoir may contain an electrode for pumping the contents. The reservoir contents may be replenished by catheters or feeder tubes connected to an external reservoir. The reservoir may take many shapes, such as tubular, spherical, hemispherical, cubic, combination thereof, or the like, depending upon the manner of fabrication, ease of forming the shape, the desired volume and the size of the unit. The reservoirs will have a capacity of at least about 1 pL, more usually at least about 5 pL and not more than about 500 pL, usually not more than about 100 pL. The devices may have a single or multiple reservoirs containing different fluids. When multiple reservoirs are present in the devices, the contents may enter a central mixing reservoir before discharge of the contents through the aperture.

Secondary reservoirs may also be present to accept the liquids that exit a first reservoir, the active agent or other liquid, and are in excess of the liquid that exits the aperture. The two reservoirs will be connected by a channel that has the aperture between the two reservoirs. Thus flow from a first reservoir will move to the aperture and be completely or only partially released through the aperture.

In conjunction with a reservoir comprising an electrode will be a pressure compensating means. This may take the form of an opening or vent connected to the reservoir. Alternatively, if one wishes to have a sealed system, except for the aperture, such a capability can be readily achieved with a variety of know devices, such as bellows, balloons, pistons, diaphragms, etc., where the enclosed device has a liquid that vaporizes as the pressure is reduced by expression of the reservoir contents into the surrounding area. In fact, the flow regulating means can be the expansion of such a mechanism with gas formation by electrolysis. These devices can be readily miniaturized and introduced into the reservoir before sealing the reservoir or a diaphragm can be a wall of the reservoir, so as to expand until it collapses against the other wall(s) of the reservoir as the reservoir contents are expressed.

Channels

Channels will generally have a width of about 1 to 100μ, more usually of about 1 to 50μ and a cross-sectional area in the range of about 1 to 250μ$^2$. The length will vary in relation to the nature of the device, the desired distance from the reservoir to the aperture, and the like, generally ranging from about 0.5 to 10μ long, more usually about 2 to 6μ long. Channels may have a variety of configurations, and feedback arms to control the flow. Channels may have any shape, for example, linear, serpentine, arc shaped and the like. The cross-sectional dimension of the channel may be square, rectagular, semicircular, circular, etc. There may be multiple and interconnected channels to provide for recirculation, mixing, moving slugs of fluid from an intersection, etc. Channels may contain electrodes for pumping the fluid.

The device may employ designs used with separation microfluidic devices. These devices employ small reservoirs and micro channels, where the electrodes contact the contents of the reservoirs. In the subject devices, it is permissible to have the electrodes in the channels. For the subject devices, there may be from 1 to 4 or more reservoirs depending upon the particular design. For example, there may be a single reservoir and a channel, where one electrode is in the reservoir and the other electrode is in the channel downstream from the aperture. A vent smaller than the aperture would be provided in proximity to the reservoir electrode to release any gas that formed. This device can provide for continuous flow of the agent from the reservoir or intermittent flow when the electrodes are activated intermittently. There would be a single solution in the device, where the agent may diffuse continuously through the aperture to provide a basal level for the agent and the amount could be increased with the activation of the electrodes.

Another design would include two reservoirs with electrodes in each reservoir and the aperture between the reservoirs. This would operate in a similar manner as described for the single reservoir. One would fill the reservoirs and channel with buffer and then add agent to the upstream reservoir. Upon activation of the electrodes one would move the agent in the reservoir to the aperture. As the agent diffused through the aperture, it could be replenished by activation of the electrodes and the process repeated intermittently, as required.

Alternatively one could introduce greater flexibility into the device by having 3 or 4 reservoirs, where one has a channel normal to a central channel or orthogonal channels on opposite sides of the central channel, each channel having a reservoir at each of the channel termini. Electrodes would be present in each of the reservoirs. One would usually have different compositions in one reservoir of the central channel and a reservoir of the side channel. In this way, different compositions could be moved to the aperture.

For example, in one embodiment, one could have buffer in the reservoirs of the central channel and the agent composition in a reservoir of a side channel. Buffer would be present at the aperture. When one wished to move the agent to the aperture, the electrodes in the reservoirs of the side channel or if there is only one arm, then the electrode at the downstream end of the central channel and the electrode in the reservoir of the side channel would be activated. One or more of the electrodes could be at zero voltage or ground. This would move the agent to the area where the channels connect to create a slug of agent at the intersection. By changing the voltages, the slug would then be moved to the aperture where the agent could diffuse out or exit the aperture. If one wished to actively move the agent through the aperture, by having an electrode at the aperture or having a dead end at the downstream terminus, the agent would be actively pumped through the aperture.

Aperture

The ASC has an aperture that permits the release of the bioactive agent present in the bioactive agent-containing reservoir. The aperture may have an opening flush with the device surface or recessed, so as to be flush with the bottom of a well. The aperture is usually connected to the reservoir by a channel. The size of the aperture will be about 0.25 to 5μ in diameter, usually about 1 to 3μ in diameter. That is, a cross-section in the range of about 0.75 to $15\mu^2$, usually about 1.5 to $10\mu^2$. Electrodes may be placed in proximity to the aperture to regulate the flow of the bioactive agent. In one embodiment, recording electrodes may be placed in or near the aperture, permitting simultaneous electrical recording and chemical stimulation of neurons.

By varying the cross-section of the channel, the fraction of the stream that exits the aperture can be controlled. By reducing the cross-section of the channel downstream from the aperture, introducing a partial block, or other expedient, the stream of the bioactive agent can be divided between exiting the aperture and continuing along the channel. This gives greater assurance of the exiting of the bioactive agent through the aperture and allows for a waste reservoir to receive the excess bioactive agent or buffer.

Reservoir Contents

The device will provide for the delivery of bioactive agents or bioagents, such as neuromodulatory agents, which include neurotransmitters, hormones, ions, messenger molecules, nucleic acids, nucleic acid vectors, drugs, etc. The ASC regulates chemical synaptic transmission by administering a controlled pulsed dosage of a biologically active agent. The ASC may form both excitatory and inhibitory stimulus at neuronal junctions. Reservoirs may contain any combination of a bioactive agent, and a buffer. The bioactive agent present in a reservoir may include any combination of neuromodulatory agents, for example, neurotransmitters, hormones, ions, messenger molecules, or liposomes. Neuromodulatory agents include, for example, amino acids, such as glutamate, aspartate, and glycine; N-methyl-D-aspartate, α-amino-3-hydroxy-5-methyl-4-isoxalonepropionic acid (AMPA), quisqualate, kainate, and anlogs thereof; gluaminergic and glycinergic agents; cholinergic agents, such as acetylcholine, suberyldicholine, analogs thereof, etc.; catecholamines or adrenergic agents, e.g.dopamine, L-dopamine, norepinephrine, epinephrine, etc., histamine serotonin and serotonergic agents; γ-aminobutyric acid and GABA-ergic agents; taurine, octopamine, nucleotides e.g., adenosine triphosphate, adenosine diphosphate, guanosine triphosphate, or guanosine diphosphate, cyclic nucleotides, messenger agents, such as peptide hormones, e.g. enkephalins, dynorphin, endorphin, ACTH, vasoactive intestinal peptide (VIP), etc; steroid hormones and active ions, e.g. $Ca^{+2}$, $Zn^{+2}$, $K^{+}$, etc.

Importantly, neuromodulatory agents include all agents that affect the receptors present on neurons. These include agents that modify the receptors, including, and not limited to, glutamate receptors, NMDA-receptors, AMPA-receptors, glycine receptors, dopamine receptors, acetylcholine receptors, and acetylcholine receptors. The bioactive agent may be in combination with a buffer, for example, phosphate buffered saline, HEPES-buffered saline, MOPS-buffered saline, Dulbecco's Modified Eagle's medium, or bicarbonate-buffered saline. Neuronal cells that can be affected include unipolar cells, bipolar cells, ganglions, pyramidal cells, glial cells, astrocytes, motor, Purkinje cell, horizontal cell of Cajal, etc.

Included among the bioagents are channel forming molecules, such as α-hemolysin, gramicidin, alamethicin, etc., sugars, dyes, sources of cellular energy, etc. The bioagents may be present as micelles, liposomes, biological membrane preparations containing ion channels and/or receptors, etc., where the bioagents containing membrane may fuse with the cellular membrane.

Flow Regulation

The ASC provides a flow regulator for controlling the administration of the bioactive agent. The flow is regulated to deliver a pulse of the bioactive agent, through the aperture at the delivery site, to modulate, e.g. excite or inhibit, a neuronal response. The flow regulator may take any form that allows for controlled flow of the bioagent through the aperture, employing electrodes to govern the flow. A controller for the electrodes may be an electronic device having an independent electrical power source to actuate the flow regulator, e.g. battery, or photodiodes that respond to incident light. Flow regulators may take the form of a mechanical pump, for example, a piezoelectric, pneumatic, electrostatic, peristaltic, piston, electromagnetic pump, or the like. Non-mechanical forms of pumps include, for example, acoustic, electric, magnetic, or electroosmotic pumps. Microfabricated pumps may be found in Andersson, et al., Sensors and Actuators B 72:259–602 (2001); Morf, et al., *ibid* 72:273–82 (2001); and Zeng et al., *ibid* 82:209–12 (2002). In a preferred embodiment, an electroosmotic pump is used to regulate the flow. Electrical wires which can be provided on or in the upper layer of the housing, connect the controller to the electrodes, and convey the electrical current to the reservoir, channel or other appropriate site.

For EOF flow regulation, a polar solution comprising salt(s) results in a double layer along a polar wall. By applying a potential along the channel, movement of the ions along the wall moves the fluid down the channel. The flow of the fluid results in discharge of at least a portion of the stream of the polar solution through the aperture.

Light sensitive polymers may also find use. A photosensitive polymer membrane can be deposited via electrochemical deposition or other means to form at least a portion of a reservoir wall or a barrier to flow. The photosensitive polymer will respond to light by swelling, contracting, or local bending, depending upon the nature of the polymer and construct, resulting in fluid flow. This can be used in conjunction with maintaining a mild positive pressure on the fluid, using an enclosed area with a liquid having a boiling point below the ambient temperature and being partially in the gas state. By swelling locally, larger pores created in the polymer matrix would allow molecules to be released at a greater rate than when not activated by light. Conversely, contraction of the polymer film would result in a reduced rate of chemical transport across the membrane. Polymers that display such properties have been synthesized and characterized. For example, a poly(diazophenylene)-based polymer gel has been shown to undergo a significant swelling/contraction transition in response to light in the visible range. In addition, the release of small peptides from a polymer network including dimethylacrylamide (co-polymerized with phenylazophenyl acrylate and phenylazophenyl acrylamide) has been reported to be capable of being triggered by light.

Mechanical work, such as bending, of a polymer membrane in response to light could also be used as a mechanism to drive bioagent delivery in a spatially-controlled manner. By bending (inward to the device) locally, expansion of the polymer would cause some fluid or solute to pass through the film and subsequently be pushed away from the device when the polymer relaxes. Alternatively, if the polymer is placed underneath the reservoir, local bending of the membrane could be used to push fluid through an aperture or thin film above the reservoir. Polymers that are able to convert light into mechanical work have been developed, such as a spiropyran photochromic compound derivative to a polypeptide, where its reversible bending characteristics in response to light and dark have been characterized. The actual response of these light-sensitive polymers can be tailored by varying their physical and chemical properties, while the time-scale of release can be fine-tuned by altering the thickness of the film.

Although electrically- and light-sensitive polymer systems have been developed, the abundance and characterization of these systems documented in the art is substantially less than those of pH- and thermo-responsive polymers. One may therefore use these polymers in conjunction with systems that provide for pH or thermal changes. For example, local electrodes placed on a film of a pH-responsive polymer providing reversible electrolysis with a change in pH, would alter the release profile of bioagents through the matrix. Analogously, chromophores covalently attached to a film of a thermo-responsive polymer could absorb visible light and dissipate the reaction energy in the form of heat, thus altering the local temperature and release of a bioagent.

In another embodiment, a membrane is deflected under an aperture to push fluid through the aperture. By placing electrodes on the membrane and the solid support under it, a potential placed across the electrodes will cause the membrane to deflect. This potential difference can be created using a photodiode, allowing light to activate the device. Additionally, a flexible membrane made of an elastomer, e.g. PDMS, can be used as a valve. The membrane covers or plugs an aperture until activated. Upon activation, the membrane is moved out of the way to allow fluid to move through the aperture. By having the fluid under mild positive pressure and controlling the time and degree to which the aperture is open, the flow of the fluid is controlled.

Pressure wave stimulation can also find use. For cells that are receptive to movement, i.e. cells that have mechanoreceptors, the above techniques can be used in pressure-wave stimulation. Actuation of the device creates a fluid flow past the cells that leads to stimulation due to protein receptors designed to sense motion. Stimulation of this sort can be used with retinal pigment epithelial cells (RPE cells).

Electrical Sources

Electrodes and connecting wires are formed by any conductive material, for example, metals or metal oxides, such as platinum, palladium, iridium, iridium oxide, titanium nitride, silver, silver chloride, chromium, tin, indium, indium tin oxide, zinc oxide, gold, or aluminum. The device may contain a single electrode pair or a multiplicity of electrodes or electrode pairs.

In place of an independent electrical source, such as a battery, photodiodes can be plated at any convenient sites to provide for an electrical source for the flow regulator, particularly, where the transparent nature of the material allows for light, e.g. from the eye, to irradiate the photodiodes and create a current. The photodiodes may be formed at the ports on opposite sides of the aperture or other site.

Fabrication

Microfabrication is readily employed for construction of the device. Standard silicon process techniques are readily adapted for producing the subject devices. Using low-pressure chemical vapor deposition, silicon nitride is grown on the surface of <100> orientation silicon waters. A combination of lithography to define the structures in a photosensitive polymer is followed by plasma etching to pattern the structures in the silicon nitride to create apertures on one side of the wafer and an etchant masking layer on the other side. An anisotropic etchant, such as tetramethylammonium hydroxide (TMAH) is used to remove the silicon along the {111} crystal plane, leaving the silicon nitride unaffected. This results in a via opening (a connecting passageway) beneath the aperture, exposing the silicon nitride membrane and completing the processing. Although not shown, the other side of the aperture is connected to a microchannel reservoir that is made by sealing a PDMS stamp with microchannels to the underside of this substrate.

The conduit or via opens into a microfluidic channel that serves as a reservoir for bioagents. The microfluidic channel is made from a standard PDMS stamp and sealed to the wafer. Such a microfluidic channel can be readily sealed to the wafer with a stable seal. The PDMS stamp having a channel is bonded to a silicon nitride surface after acid cleaning (e.g. HCl) and plasma treating, forming an irreversible bond. The resulting channel can serve as a general-purpose buffer reservoir for dealing with waste products and for delivering bioagents. Apertures may be formed smaller than the length scale of a neuron to insure that only a single cell is stimulated.

Methods for microfabrication or nanofabrication are described in U.S. Pat. Nos. 5,776,748, 5,900,160; 6,060,121; and 6,180,239; and such articles as: "Patterning of a Polysiloxane Precursor to Silicate Glasses by Microcontact Printing," Marzolin, et al., Thin Solid Films 1998, 315, 9–12; "Microfabrication, Microstructures and Microsystems, "Qin, et al., In: Microsystem Technology in Chemistry and Life Sciences, vol. 194, Manz, A and Becker, H eds., Springer-Velag, Berlin, 1998, 1–20 and "Unconventional Methods for Fabricating and Patterning Nanostructures," Xia, et al., Chem Rev 99:1823–48 (1999). All patents both supra and infra, are hereby incorporated by reference in their entirety. Electrodes and other elements may be formed using techniques known in the art, e.g., sputtering and controlled vapor deposition methods followed by chemical etching, and the like.

Figure 2:
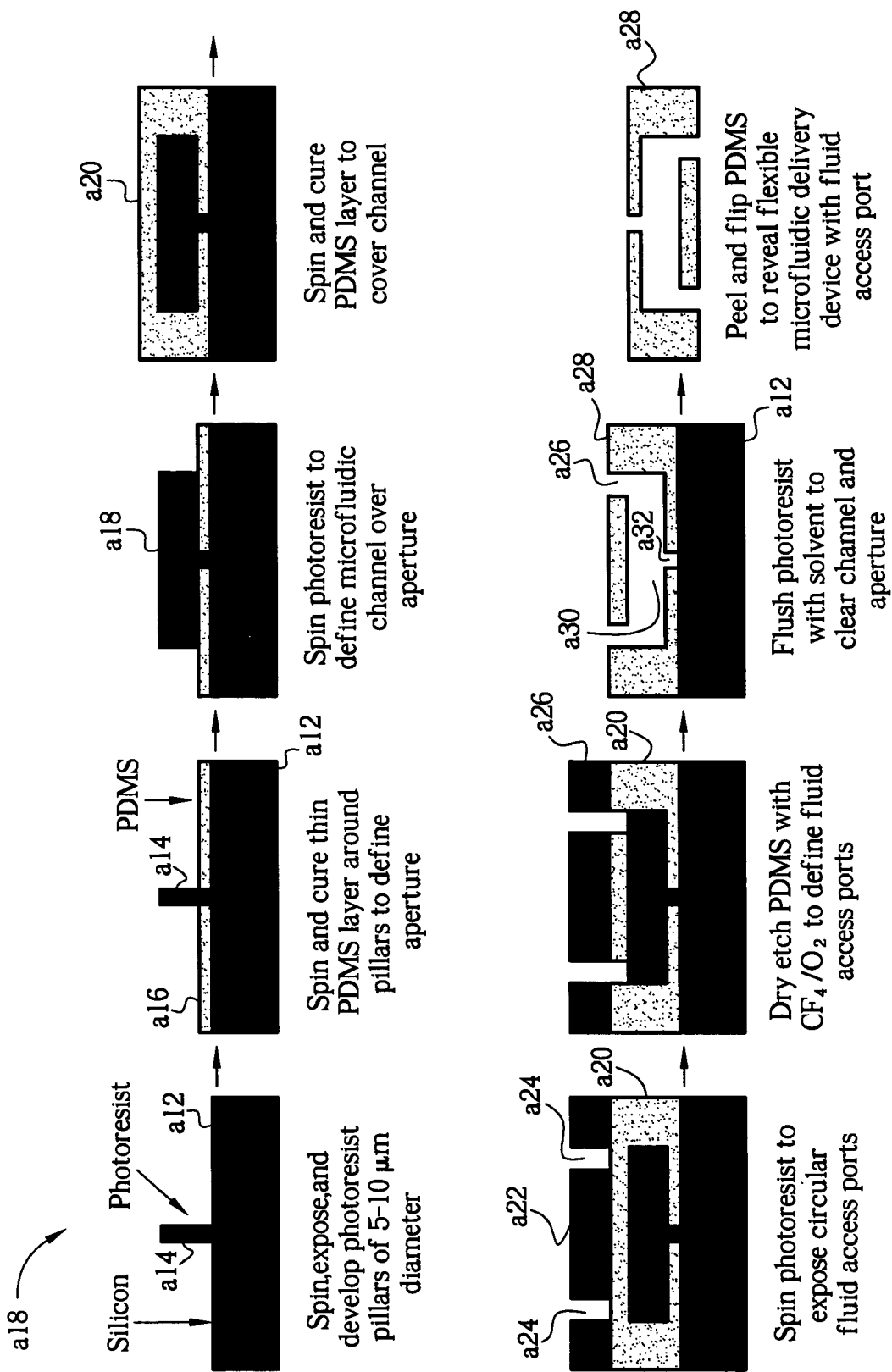
FIG. 2 is a diagram of the various stages in the microfabrication of the device.
Figure 3:
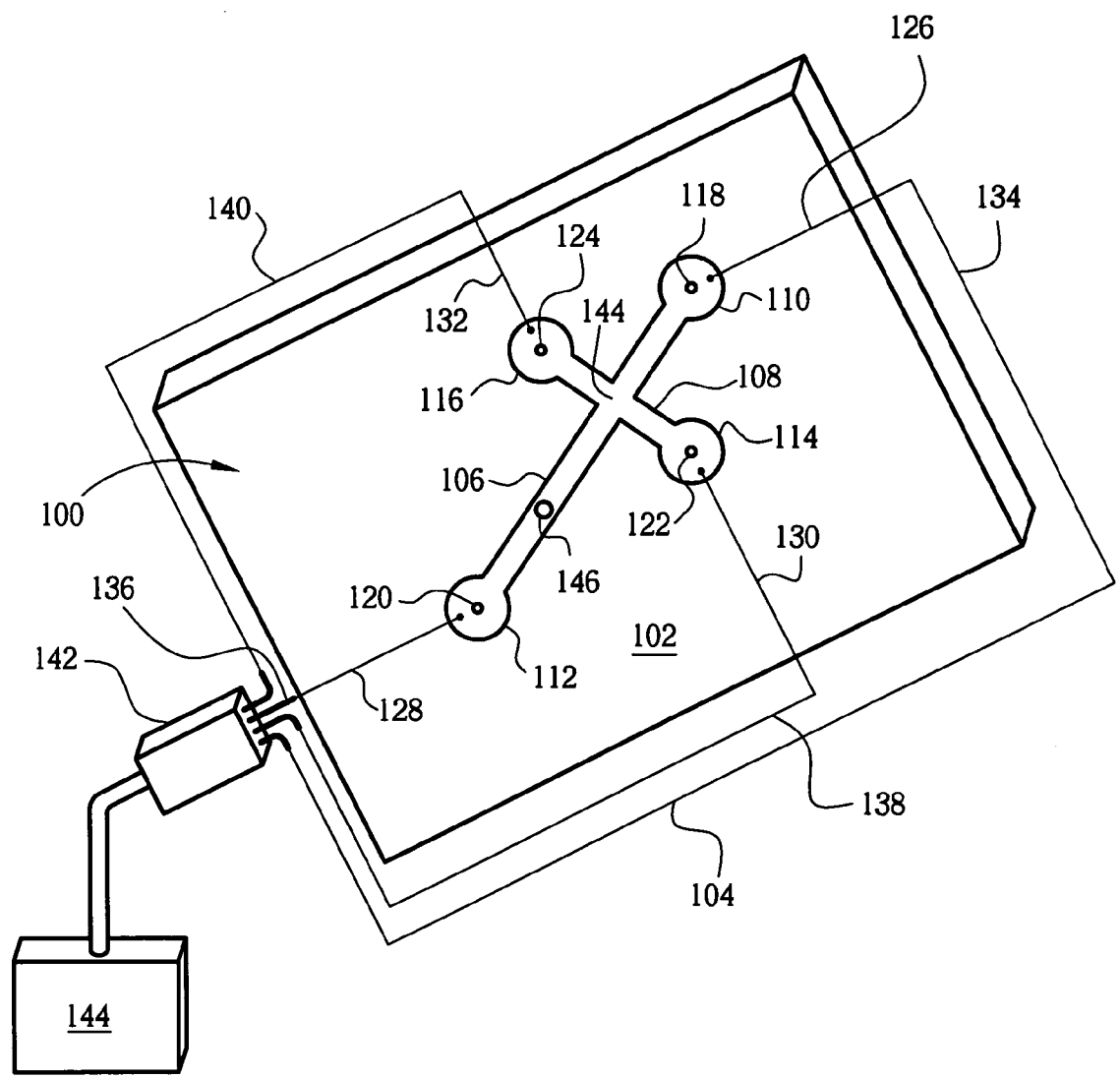
FIG. 3 is a perspective view of a subject device with a plurality of channels and reservoirs.
Figure 4:
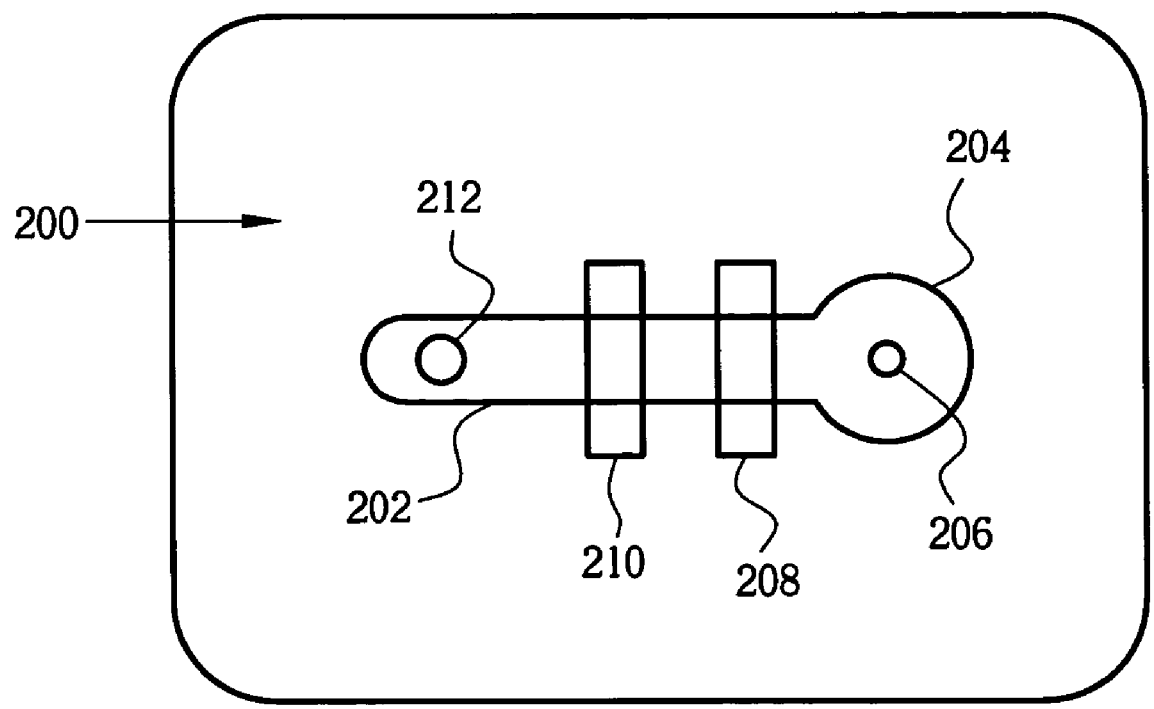
FIG. 4 is a plan view of a single channel device with photodiodes.
Figure 5:
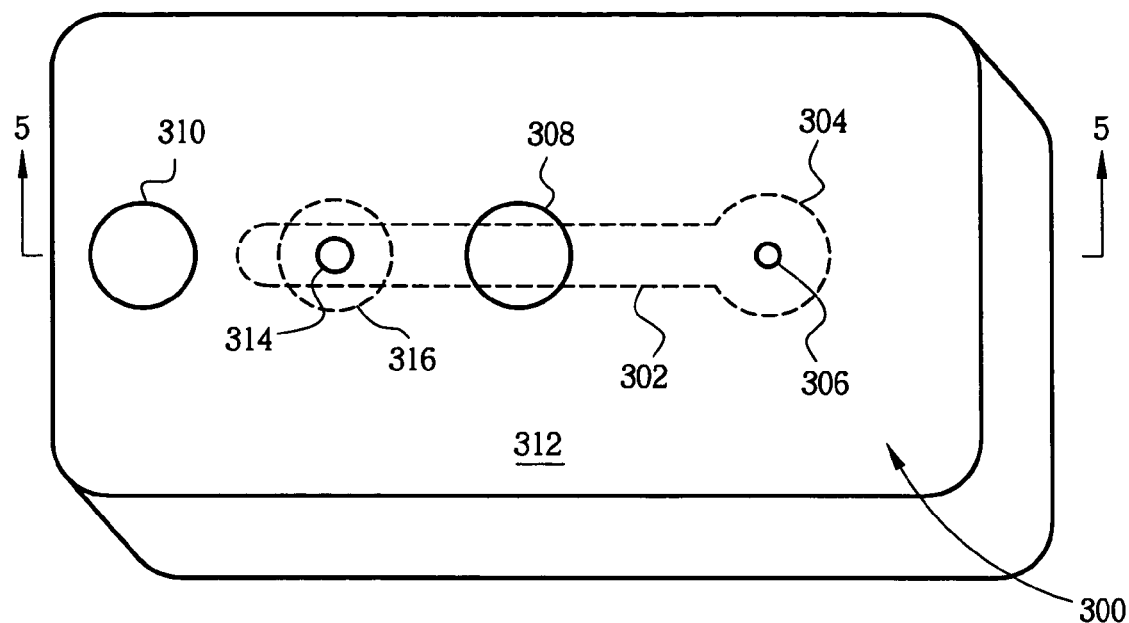
FIG. 5 is a plan view of a device with piezoelectric control of a diaphragm for pumping.
Figure 6:
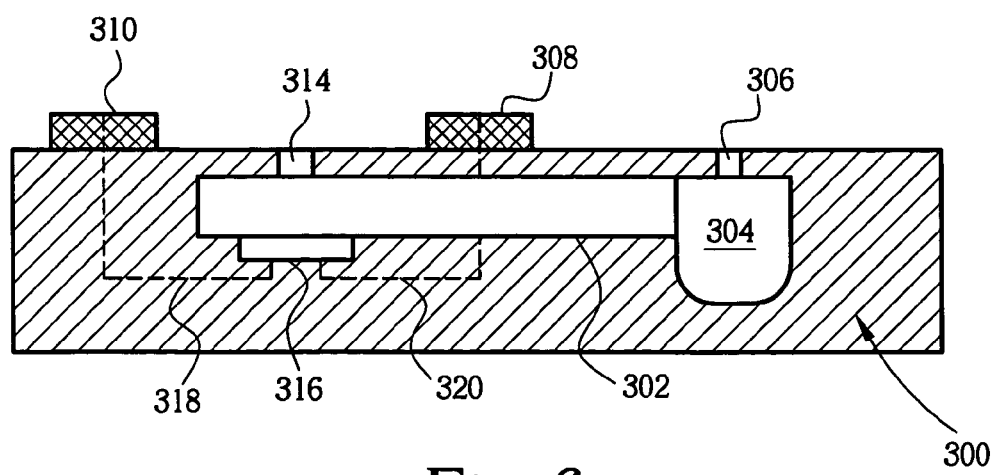
FIG. 6 is a cross-sectional view of the device of FIG. 4 along line 5—5.

The fabrication can follow the procedure described in FIG. 2. The device is prepared from any convenient soft material exemplified by PDMS in FIG. 2. The method uses a silicon chip and microfabrication with photolithography as developed for transistors and microprocessors. A flow diagram a10 begins with a silicon chip a12 that has been etched to provide a pillar a14 of about 5–10μ diameter that will serve as the mold to form the aperture in the device. After forming the pillar a14 a thin PDMS layer a16 is formed by spinning and curing. The pillar a14 is eroded away to form the aperture. A layer of photoresist a18 is formed by spinning and curing a photoresist to define the microfluidic channel and aperture. A PDMS layer a20 is then spun and cured where the future channel is covered. Using photoresist to form a top layer a22, by selective curing circular fluid access ports a24 are exposed for further etching. The PDMS layer a20 is then dry etched with $CF_4/O_2$ to define fluid access ports in the PDMS layer. The photoresist a18 and a22 is then removed with solvent to provide device a28 with channel a30 and aperture a32. The device may then be pealed from the silicon chip a12. Not shown are electrodes that can be plated at the ports.

Figures

Figure 1B:
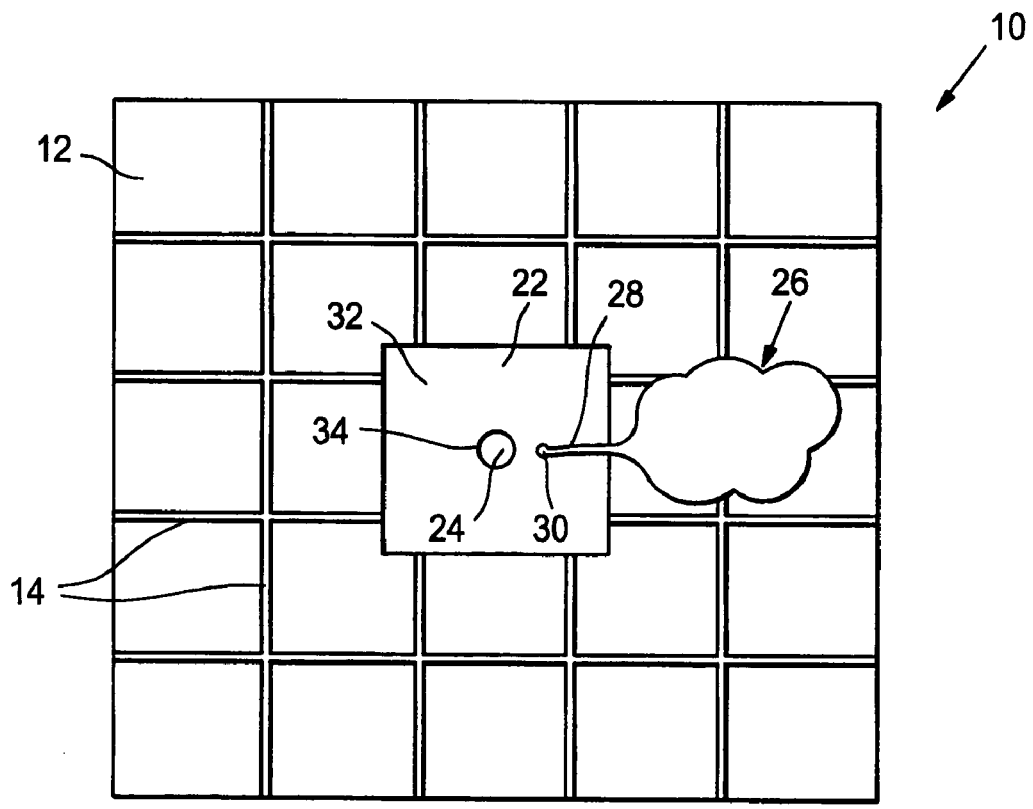
FIG. 1B is a plan view of the artificial synapse chip of FIG. 1A.

In FIG. 1A directed growth of a cell process on a device embodying features of the subject invention are depicted. A cell 26, with a cell process (neurite 28 with a growth cone at its tip) is shown in contact with substrate 12 and micropattern 14. The path followed by the neurite 28 and growth cone 30 on substrate 12 is guided by micropattern 14 so that neurite 28 and growth cone 30 are led to recess 22 and aperture 24. Recess 22 in the substrate 12 leads to an aperture 24 that forms a passage across the supporting layer 16. As shown in FIG. 1B, the floor 32 of recess 22 is formed of supporting layer 16 free of overlying substrate 12. Aperture rim 34, in supporting layer 16, surrounds aperture 24, and defines the passageway through supporting layer 16. Although only one cell and only one neurite is shown in FIG. 1A, it will be understood that a plurality of cells, neurites and growth cones may be in contact with substrate 12, recess 22 and aperture 24. A neurite may be directed by the path of micropatterned growth factors to a microfabricated aperture 24, as shown in FIG. 1A.

Figure 1C:
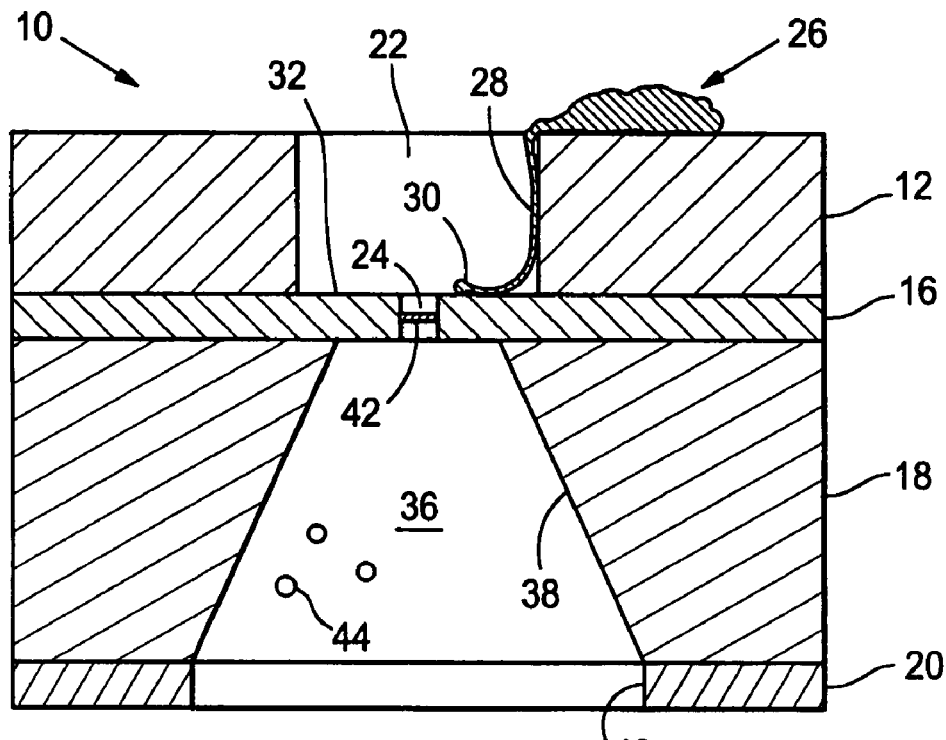
FIG. 1C is a cross-sectional view of the artificial synapse chip of FIG. 1A taken along plane 1C—1C.
Figure 1D:
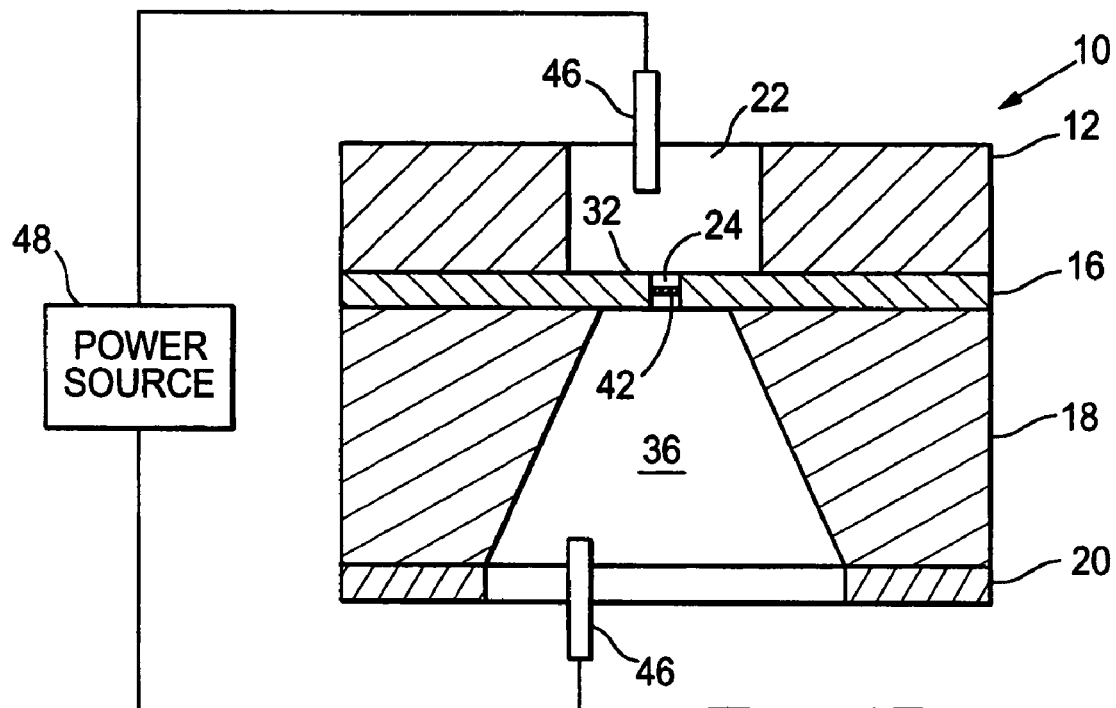
FIG. 1D is a cross-sectional view of an artificial synapse chip as in FIG. 1A taken along plane 1C—1C, illustrating an embodiment of the invention having electrodes.

In the cross-sectional views depicted in FIGS. 1C and 1D taken along plane 1C—1C of FIG. 1A, aperture 24 opens into reservoir 36 defined by wall 38 of the intermediate layer 18 and wall 40 of the base layer 20. A membrane 42, such as a lipid bilayer membrane, may be formed across aperture 24 to separate reservoir 36 from recess 22. The membrane 42 across aperture 24 may prevent substantially all passage of material between recess 22 and reservoir 36 prior to operation. However, membrane 42 may be semi-permeable effective to regulate the passage of material through aperture 24 without completely preventing passage of material. By employing a semi-permeable membrane that allows the passage of defined materials, such as a lipid bilayer membrane containing channels, transporters, etc., the defined materials will be able to be discharged from the reservoir. Lipid bilayer membranes may be formed by Langmuir-Blodgett techniques, e.g. Montal and Mueller, *Pro. Nat. Acad Sci USA* 69:3561–66 (1972); Montal, *Meth Enzymol* 32:545–56 (1974); and Lindstrom, et al., *J Biol Chem* 255:8340–50 (1980). A lipid bilayer membrane can be used with liposomes carrying bioagents, where the liposome will fuse with the membrane to release its contents into the recess 22.

Recess 22 and reservoir 36 may each contain a solution: the solution in recess 22 may be the same or different from the solution in reservoir 36. The solutions are normally physiological solutions, that may contain bioagents. Solutions that find use include saline, phosphate- or carbonate- or HEPES buffered saline, Dulbecco's Modified Eagle's Medium, etc.

The solutions containing bioagents in the recess 22 and/or reservoir 36 will have access to aperture 24 and membrane 42. The aperture 24 may be a stimulation site effective to stimulate a cell by bioagent interactions. The stimulation site can be very specific to a single cell 26, such as a neuron, and mimic the length scales of chemical synapses or gap junctions in the body.

Bioagents 44 may regulate the permeability of the membrane 42 or may be capable of contacting and fusing with membrane 42 effective to deliver bioagents to the recess 24 from the reservoir 36 or from the recess 24 to the reservoir 36. The bioagents will generally be present in reservoir 36 and the bioagents may take many forms as described above.

A device containing electrodes is depicted in FIG. 1D. Electrodes 46 are used to carry electrical signals from power source 48 to supply current or impose a voltage between electrodes 46 to stimulate cell 26 or modulate its activity.

Figure 1E:
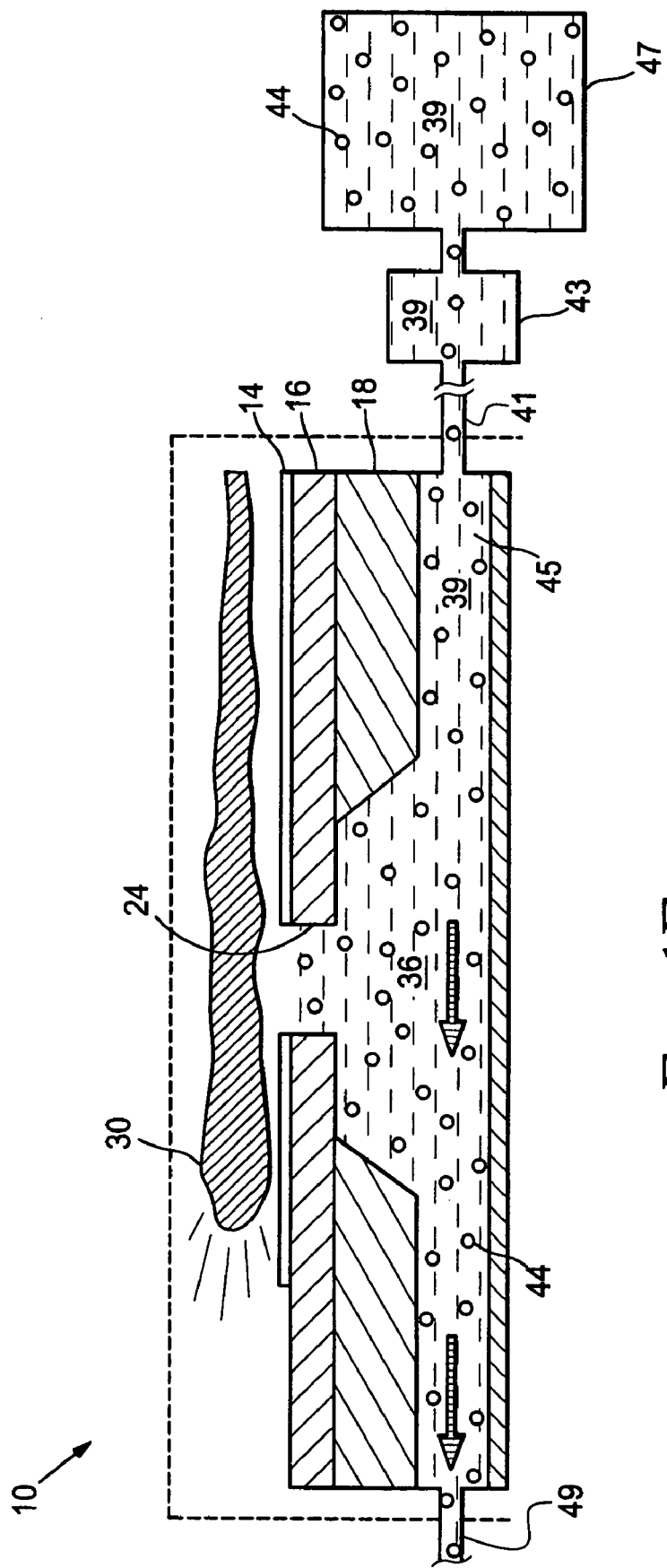
FIG. 1E is a cross-sectional elevation view of a system having a pump and a depot for holding a store of solution and including an artificial synapse chip.

The ASC 10 shown in FIG. 1E is part of a system including a fluid conduit 41 configured to carry a fluid 39 (with fluid flow optionally induced by a pump 43) to a microfluidic channel 45 for delivery to reservoir 36 and aperture 24. A biocompatible fluid 39 is stored in a depot 47 operably connected to pump 43 and microfluidic channel 45 by fluid conduit 41. A fluid outlet 49 may be used to drain or remove excess or waste fluid into a waste reservoir, not shown.

Figure 1F:
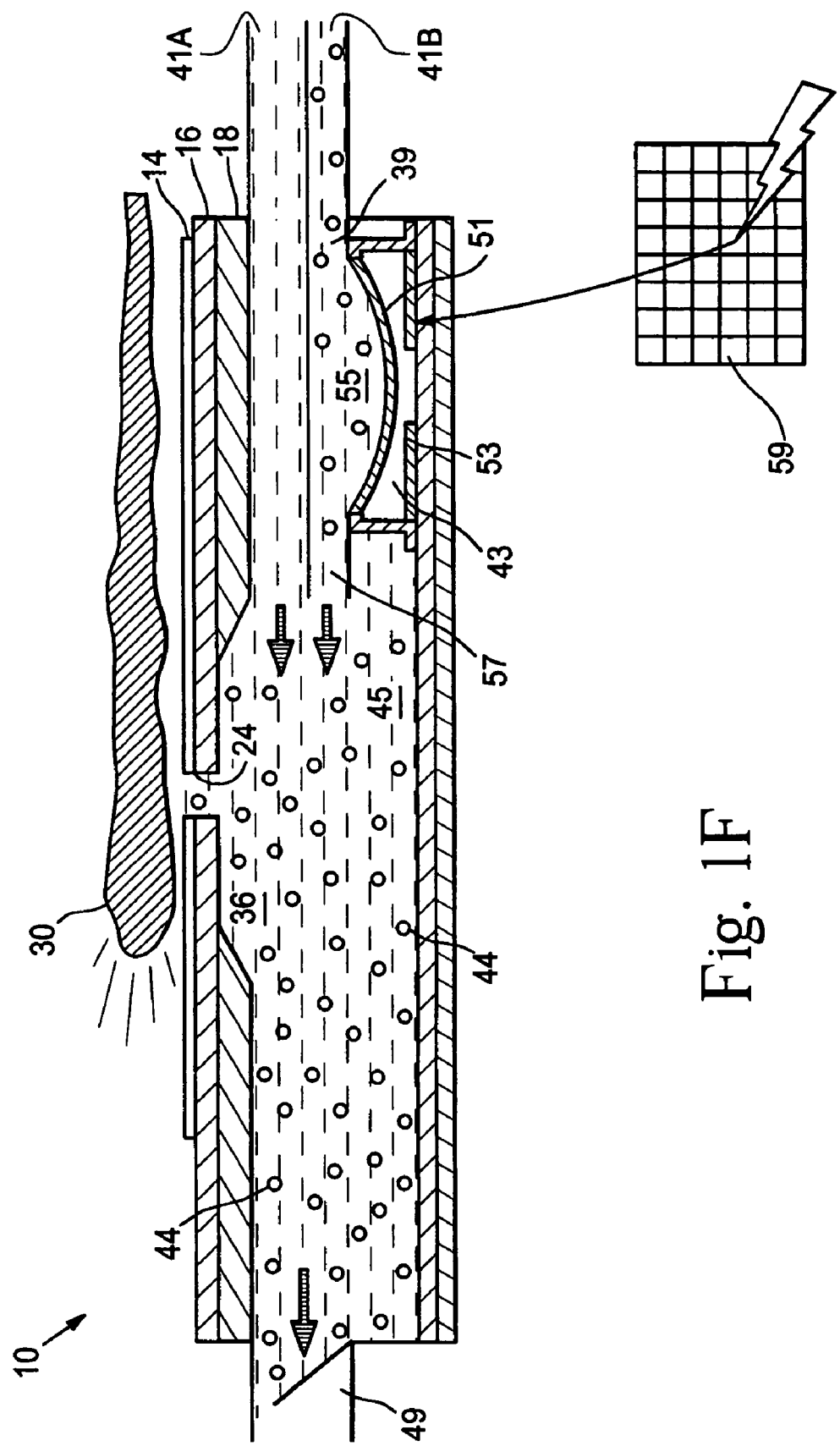
FIG. 1F is a cross-sectional elevation view of a portion of a system having a pump including an artificial synapse chip.

In FIG. 1F, a system is depicted including an ASC 10 having a cell with growth cone 30 growing over a pattern 14 on s a silicon nitride substrate 16, and a fluid conduit 41 comprised of two parts, a buffer inlet 41A and a transmitter inlet 41B. Not shown are a depot 47 containing transmitter solution connected to transmitter inlet 41B. The pump 43 illustrated in FIG. 1F is a micro-electro-mechanical (MEM) pump similar to those used in ink-jet printers to eject drops of fluid. Such pumps are described in, for example, U.S. Pat. No. 5,734,395. A MEM pump as illustrated in FIG. 1F includes a silicon diaphragm 51, a counter electrode 53, and a microfluidic channel 55 built over the diaphragm structure. The region of the microfluidic channel 55 above the diaphragm 51 is filled with fluid 39 and in fluid continuity with a depot 47 (not shown). Initially, the diaphragm 51 is in a horizontal (undeflected) configuration. The application of a minute bias voltage between the diaphragm 51 and the counter electrode 53 is effective to deflect the diaphragm 51 downward as shown inf FIG. 1F, thereby increasing the volume of the microfluidic channel 55 region above the diaphragm 51 and drawing fluid 39 from the depot 47 along transmitter inlet 41B. Removal of the bias voltage allows the diaphragm 51 to relax back to its initial position, forcing fluid out of microfluidic channel 55 and towards reservoir 36 and aperture 24. The bioagents 44 in fluid 39 are transported to reservoir 36 and can diffuse into reservoir 36 and aperture 24 to contact growth cone 30 and modulate the activity of the cell. In this way, a brief pulse of a bioagent may be delivered to a cell having a process in proximity to the aperture 24.

In embodiments of ASCs, conduit 41 would include transmitter inlet 41B; in other embodiments, such as the one illustrated in FIG. 1F, conduit 41 also includes a buffer inlet 41A. Flow of buffer solution through buffer inlet 41A serves to flush out the microfluidic conduit with buffer, removing bioagents 44 from the aperture 24. Such flushing prepares the system for a subsequent pulse of bioagent 44 and terminating the effect of the bioagent 44 in the prior pulse.

Diffusion of the bioagent 44 through aperture 24 can be very rapid due to the thinness of the aperture, which may be about 500 nm thick. The diaphragm 51 of an MEM pump 43 may flex at high frequency, so as to eject fluid 39 at high frequency. The pulses may be delivered at frequencies in the range of about 1 Hz to 1000 Hz, generally not more than about 500 Hz. Such rapid signaling matches the rapid signaling rates found in vivo in the brain and retina.

In selecting the concentration of the bioagent in the fluid, consideration will be given to the MEM ejector pulsing frequency, fluid flow rate through the microfluidic conduit, and in the case of EOF, the voltage employed. Also, where fluid is not discharged, the diffusion rate of the bioagent through the aperture will be considered. The size of a pump, such as the ejector diameter determined by the diameter of the outlet 57 of transmitter inlet 41B can range from between about 1μ to 500μ, where the size will be selected in conjunction with the required capacity of the microfluidic channel.

The performance of a pump 43 and the system illustrated in FIG. 1F depends on the design of the system, the materials used and the fluids employed. The damping experience by the system is related to several factors, including fluid viscosity, the geometry of the microfluidic conduit 45 and channel 55, as well as the geometry of the other components. Exemplary of a subject device is one configured with a diaphragm 51 comprised of polysilicon, a narrow microfluidic channel 55 and a small initial separation between the diaphragm 51 and the counter electrode 53. Since there is no threshold voltage for activating the motion of a polysilicon diaphragm, a MEM ejector pump can deliver volumes as small as attoliters, or even zeptoliters. The power required to charge a capacitor of the size of a diaphragm 51 to a fraction of a volt is about a picowatt. A single photodiode, such as an avalanche photodiode capable of generating nanoWatts of power is thus able to charge hundreds or even thousands of such MEM pumps to deliver bioagents to cells.

The power to actuate a pump 43 may come from a photodiode in a photodiode array 59 as illustrated in FIG. 1F. Light contacting such an array 59, which may be from external light or an LED activated externally by an electrical source, is effective to actuate a pump 43 configured to pump a bioagent containing fluid 37 into a microfluidic conduit 45 where the bioagents are transported to the aperture 24 and diffuse through the aperture 24, transducing a light signal into a biological signal.

In FIG. 3 a multichannel device 100 is depicted. The device has an upper layer 102 and a lower layer 104. In lower layer 104, crossing trenches 106 and 108 are formed that are closed by upper layer 102 to form channels. Trench 106 joins reservoirs 110 and 112, while trench 108 joins reservoirs 114 and 116. In upper layer 102, vents 118, 120, 122 and 124 provide for the release of gas from reservoirs 110, 112, 114 and 116, respectively. Electrical ribbons 126, 128, 130 and 132 are plated onto upper layer 102 and provide electrical contact with the contents of reservoirs 110, 112, 114 and 116, respectively and are connected by wires 134, 136, 138 and 140, respectively to a conduit 142 that connects a central electrical source and data processing unit 144 to the electrical ribbons 126, 128, 130 and 132.

The procedure and structural organization is described in U.S. Pat. Nos. 5,858,187; 6,033,546; and 6,221,226 and U.S. Patent application No. 2003/0150733. One has buffer in reservoirs 110 and 112 and agent in buffer in reservoir 114. One moves agent across the intersection 144 of the channels so as to fill the intersection 144 with buffer. The voltages are then switched so that buffer is moved from reservoir 110 toward reservoir 120 moving the agent at the intersection 144 to aperture 146. The slug of agent at the aperture is then allowed to diffuse out of the aperture 146 into the area surrounding the aperture. If positive pumping were desired, another electrode would be provided at the aperture to direct the agent through the aperture by causing the fluid to flow through the aperture.

In FIG. 4 device 200 is depicted, where the material is a block of clear flexible biocompatible plastic. The device has channel 202 connected to reservoir 204 with vent 206. Oppositely doped photodiodes 208 and 210 electrically contact the fluid contents of channel 202. In operation, the channel 202 and reservoir 204 are filled through aperture 212. The device is implanted at a site where it can be exposed to incident light. When the photodiodes 208 and 210 are activated, the fluid in the channel 202 is pumped through the aperture 212 and replenished in the channel 202 from the reservoir 204.

In FIGS. 5 and 6, device 300 uses a piezoelectric transducer and a diaphragm for pumping the agent. These systems are amply described in U.S. Pat. Nos. 5,798,600 and 6,262,519. As before, a channel 302 is connected to reservoir with vent 306. Oppositely doped photodiodes 308 and 310 are formed on upper surface 312 or may be placed on the opposite surface or on both surfaces or one or both of the sides of the device, depending upon whether device 300 is transparent, the placement of the device in relation to the incident light, and the like. Channel 302 is connected to aperture 314. As part of the channel under the aperture 314 is a diaphragm 316, whose movement is controlled by a piezoelectric device 318. The piezoelectric device 318 is connected to photodiodes 308 and 310 by wires 318 and 320, respectively. In operation, the device 300 is placed at a site where incident light.

Methods of Use

By implanting the device adjacent neuronal cells to be affected by the active agent, the fluid from the aperture baths a region with the agent in a controlled amount. By appropriate choice of the agent, one can stimulate or deactivate neuronal cells, enhance the viability of neuronal cells, and the like. The retina is paradigmatic of the use of the subject device and will be described in substantial detail. Based on the description of the use of the subject devices with the retina, the subject devices can be adapted for use with other neuronal environments for affecting the viability and/or activity of the neuronal cells in the environment of the device. The device finds use at neuronal junctions or at neuromuscular junctions. In effect, the subject devices may act as artificial synapses or therapeutic devices.

As described in the experimental section, the subject devices can be inserted intraocularly adjacent to the retina, subretinally or epiretinally. After anesthetizing the area, a standard 3-port pars plana vitrectomy can be employed, with epiretinal implants inserted through the sclerectomy. For subretinal implants, a subretinal bleb is formed in the macular area, a retinotomy created and the implant inserted into the subretinal space. At other site, similar protocols can be employed for insertion of the implant in association with the neuronal structure.

With a bilayer membrane across the aperture, the device can be used for drug screening. By having channels or receptors in the bilayer, the effect of drugs on the opening or closing of the channels can be determined by determining the passage of ions or other molecules specifically through the channel. By having a cellular lysate in contact with the bilayer, one can determine the effect of drugs on receptors, where the lysate is effective in providing a response of the receptor to a drug.

The following examples are offered by way of illustration and not by way of limitation.

EXPERIMENTAL

Example 1

Methods for stimulating cells through the nanoaperture and measuring their activity using fluorescence from $Ca^{2+}$ sensitive dyes include the following: (1) voltage clamping of the cell to the aperture (applying suction via the microchannel) and varying the voltage of the buffer in the microfluidic channel; (2) chemical stimulation of the cell by pulsing a bolus of neurotransmitter to the under side of the cell; (3) microfluidic bolus of liposomes containing neurotransmitters to the aperture opening; and (4) microfluidic reservoir of engineered cells that would stimulate the neurite through the release of the transmitters.

A subconfluent layer of PC12 cells is cultured on an array of microapertures. Cell activity is measured by fluorescence microscopy with the cells loaded with a $Ca^{+2}$ sensitive dye (e.g. indo-1, fura-2, fluo-3, calcium green, aequorin). The fluorescence serves both to monitor the activity of the cell directly above the aperture and to see the effect on neighboring cells. The surface may be modified around the aperture to achieve a good "seal" to the cell membrane (where a good seal is mechanically stable and has an electrical resistance near to or in excess of one gigaohm). Surface modifiers may include different extracellular matrix proteins and "cell Tak® (Becton Dickinson). Stimulation techniques may depend on varying the size of the aperture, temporal and spatial resolution, chronic stimulation, etc.

A microstamp is used to make a micropattern to overlay onto an array of apertures. The micropattern directs the growth of neurites toward the aperture. Cells growing on ASC substrates are stimulated by voltage pulses from electrodes in contact with the solution in the recess and in the reservoir. The voltage pulses are effective to depolarize the cell process adjacent or across the aperture. Depolarization voltages range from about 1 mV to about 100 mV. Depolarizations between about 10 mV to about 50 mV are found to most effective.

Liposomes containing the neurotransmitter acetylcholine and adenosine triphosphate are placed in the reservoir. A lipid bilayer membrane spans the aperture. Cells with processes growing across or adjacent to the aperture are stimulated by contact with neurotransmitter released by liposomes fusing with the lipid bilayer membrane. Fusion is promoted by an osmotic gradient across the liposome membrane and across the lipid bilayer membrane. Neuronal excitation is measured using fluorescence with $Ca^{+2}$ sensitive dyes.

Example 2

A prototype neural interface device was developed that is described in Peterman, et al., supra. The basic component in the 8'8 mm device is a small circular aperture in the side of a microfluidic channel. Using standard microfabrication techniques, a thin layer of silicon nitride (1.6µ thick) was deposited on a silicon wafer. Four circular apertures were etched through the silicon nitride in a 2'2 array (5µ diameter, 125µ center-to-center). The silicon wafer was then anisotropically etched through the silicon wafer, creating a thin, free standing membrane roughly 350µ on a side. Channels were created by lithographically patterning 25µ deep SU-8 photoresist over the apertures. The 50µ wide channels were designed with a bend to allow each channel to overlay a single aperture. The bend provides sufficient room for inlet and outlet connections to each channel. Gold electrodes for controlling electroosmotic flow are patterned inside the channels with two common grounds and four control lines. The device can be readily scaled down for synaptic dimensions. For example, with a device 2.5'2, 5µ channels, 10µ apart between 1µ apertures, interdigitated electrodes 10µ apart, the power expenditure would be limited to 2 nW per channel.

Changes in fluorescent levels were observed with an upright confocal microscope (Nikon E800, 10× dipping objective 0.30 NA) with a Nikon PCM 2000 confocal unit and a Sony DXC-390 CCD color camera. For confocal imaging (of fluorescein bubbles) two lasers were used to excite the fluo-4 (Argon ion, 488 nm) and Texas Red (HeNe, 543 nm). Images were sampled simultaneously using two photomultiplier tubes (515/30 bandpass and 605/32 bandpass filters), and analyzed using SimplePCI (Compic Inc., Cranberry Township, Pa.). The Sony camera was used in conjunction with a mercury arc lamp for standard fluorescence imaging of fluid flow through the bent channels.

For the electric field driven fluid injection, the chips are mounted in an acrylic holder, consisting of an acrylic base plate with fluid access holes and a capping plate with a central hole as a fluid bath. The chip is aligned using a piece of thin, transparent silicone rubber (PDMS) as a gasket. Thin strips of aluminum foil for electrical contacts to the gold pads were placed on the PDMS gasket before the chip is aligned. Once the chip is mounted in the holder, fluid was loaded into the channels through access holes in the acrylic block using a pipettor. The holder is placed on a microscope stage, the fluidic bath is filled with an appropriate solution (e.g., Ringer's solution for PC12 cells), and electrical contact is made with alligator clips to the power supply. The electrical signals are supplied via a four channel, digital-to-analog converter (ITC 18, Instrutech, Port Washington, N.Y., controlled via Igor (Wavemetrics, Lake Oswego, Oreg.).

The numerical simulations are carried out on a Pentium 4 class PC, running Windows 2000 with 1.5 GB of RAM. The equations are solved using a finite element method in FEMLAB (Comsol, Burlington Mass.), which runs on top of MATLAB (Mathworks, Natick, Mass.). The software is supplied with the Navier-Stokes equation in addition to the electric field due to the applied potential and the electric double layer. Diffusion and convection driven concentration changes are also solved.

The channel was filled with an acidic fluorescein solution, where fluorescein strongly fluoresces at basic pH. As the fluorescein solution flows through the aperture, the solution mixes with an approximately neutral pH bath (pH 7.4) and fluoresces, appearing as a bubble with a bright rim under scanning confocal microscopy. As a time varying potential is applied to the channel (sine wave, ±2.5V, 3.125 second period), fluid is first ejected from the aperture, increasing the size of the bubble and then withdrawn back into the aperture, decreasing the size of the bubble.

PC12 cells were cultured on the surface of the chip. The silicon nitride surface is first treated with poly(d-lysine) and laminin to promote cell growth. A droplet of poly(d-lysine) at 50 μg/ml was placed over the silicon nitride window for 30 min at room temperature. After rinsing the device in PBS, the laminin was applied at 2–5 μg/ml in PBS for 8 h in an incubator (37° C., 6.5% $CO_2$). Following rinsing with PBS, the cells were ready for use.

Measurement of bradykinin stimulation was accomplished by observing changes in intracellular $Ca^{2+}$ levels using fluo-4 (Molecular Probes, Eugene, Oreg.). The cells were loaded with fluo-4 as per the manufacturer's specifications using Ringer's solution (135 mM NaCl, 5 mM KCl, 10 mM D-glucose, 2 mM $MgCl_2$, 2 mM $CaCl_2$, 10 mM HEPES, pH 7.2). The stimulating solution was a mixture of bradykinin (Sigma, St. Louis, Mo.), Ringer's solution and sulforhodamine 101 or fluorescein (Sigma). Bradykinin was reconstituted in Ringer's solution at 1 mg/ml (1 mM) and then diluted to 10μ. Sulforhodamine was reconstituted in DMSO at 8 mM and added to the stimulating solution to yield a final concentration of 4–8μ.

PC12 cells change their intracellular $Ca^{2+}$ levels upon a bradykinin stimulus. The channels were filled with a brakykinin solution (10μ in Ringer's solution) mixed with the fluorescent dyes Texas Red and/or fluorescein for visualization. Upon channel activation, a small amount of fluid is seen to eject from the aperture leading to stimulation of the two PC12 cells nearest the aperture (25μ to cell center).

Sequential stimulation was shown using different apertures. Three channels were activated sequentially in a clockwise direction (at 6.6, 19.9 and 42.0 seconds) using a computer-controlled digital-to-analog converter. At each time point, stimulation was limited to 25μ from the aperture. The time between stimulation events from different channels is long, due to the rather slow dynamics of PC12 cells.

Repeat stimulation of PC12 cells was shown as follows. Two cells were growing directly over the aperture. After applying the first pulse, the cells are seen to brighten slightly and then dim. A second pulse is applied brightening the cells again. The stimulation cycle was continued at a faster pace, each time dimming less than they brightened, finally reaching full stimulation. Maximum stimulation occurred between the first and second frames after channel activation or between 2.2 and 4.4 seconds. It was noted that the maximum ejection occurs about 1.5 sec after initiation, while PC12 cells are expected to respond to a stimulus after 1.5 sec, so that there should be a response 3 sec after activation. If the activation were due to the electric field, one would expect maximum stimulation 0.8 sec after stimulation.

Example 3

In another study, the prosthesis device material consisted of a combination of SU-8 photoresist (MicroChem Corp.) and PDMS. The device was prepared substantially as described in FIG. 2. To alleviate adhesion between the PDMS layers and the silicon substrate, a thin gold layer (100 nm) was deposited on a blank four-inch silicon wafer. A layer of SU-8 was spun on the gold at ~40μ thick as per the manufacturer's specifications. The SU-8 was exposed to define the negative of the channels. After development, PDMS was spun on the wafer at a thickness greater than the SU-8 structures. The PDMS at this point was quite flexible and self-adhesive. The PDMS was first treated in an oxygen plasma (155 W, 60 sec) and a thin layer of SU-8 was spun onto the substrate. The SU-8 layer adhered to the PDMS, stiffened the material and limited the self-adhesion. After the SU-8 was gross exposed and hard baked, the PDMS-SU-8 bilayer was peeled from the silicon wafer as a sheet.

On a second wafer, PDMS was spun to create the top of the device. Gold was first deposited as before. Then, PDMS was spun at high speed and long times to create a very thin sheet. After curing, this piece (still attached to the wafer) and the bilayer were both treated in hydrochloric acid (1:4HCl:$H_2O$) and in an air plasma (75 W, 60 sec). The bilayer was placed PDMS side down against the thin PDMS sheet, placed on a hot plate and compressed with a lead brick (~12 kg). After 30 min, the pieces were carefully peeled from the substrate.

New Zealand White rabbits (2.5–3.5 kg) were used for testing the different implants. The rabbits were anesthetized with ketamine (35 mg/kg) and xylazine (5 mg/kg) administered via intramuscular injection. Tropicamide 0.5% and phenylephrine 2.5% eyedrops were instilled into the conjunctival sac of both eyes every 5 min for three doses. Standard 3-port pars plana vitrectomy was performed. Epiretinal implants were inserted through the scleretomy using retinal forceps and released once they were in the middle of the vitreous cavity. Subretinal implants involved creating a retinal bleb in the macular area by injection of approximately 0.5 mL of balanced salt solution through a 40-gauge needle (DORC, Kingston, N.H.). A retinotomy 1–2 mm in diameter was created and the implant was inserted into the subretinal space through the retinotomy using retinal forceps. The retina was reattached by air-fluid exchange. The care of the animals conformed to the ARVO Statement for the *Use of Ophthalmic and Vision Research.*

Soft devices were used for the implants. The device (250% thick) was peeled from the wafer and cut into implantable pieces (~1.25 mm per side) using surgical scissors. The structure within the PDMS was a single straight channel with fluidic ports at both ends of the channel. The channel was roughly 4 mm long and 100μ wide. The pieces used for this study were cut across the channel in order to work with a small piece. Two pieces were implanted, one epiretinal and one subretinal. After an air-fluid exchange, the retina flattened nicely on the device.

The final implant was similar to the previous implant but lacking the SU-8 structural layer. The absence of the SU-8 layer made the device very flexible—the whole device could be rolled or folded without defect. For implantation, the piece (4.5 mm per side, <200μ thick) was folded in half. Once inside the vitreous cavity, it unfolded with no visible damage.

In accordance with the subject invention, a synthetic synapse is provided that allows for the active movement of agent into neuronal space to modulate the activity or viability of the neurons. Various agents can be used to influence the chemical activity of the neuronal cells, so as to transduce signals, provide for neurotransmitters in the region between the presynaptic and postsynaptic neurons, to modulate neuronal hyper- or hypoactivity, to provide a response to an external stimulus, such as light, to aid in evaluating neuronal responses by providing agents directly at the neuronal interactions under controlled conditions, and the like. The use of chemical stimulation, rather than electrical stimulation, provides a more natural control of neuronal response, allows for natural processes to remove the agent in the synapse, and permits the application of a plurality of agents at different times and in different amounts to regions of neuronal activity. The devices provide for controlled release of amounts of agents that can pervade small or large areas in the vicinity of the device. The devices aid in research in evaluating the neuronal response to a particular agent, e.g. drug, in acting on normal or diseased neurons. Thus, the devices can be used in screening of drugs as to their activity, where the activity of the neurons can be followed using clamps or other devices for detecting changes in the activity of the neurons. The devices find use in stimulating or inhibiting neuronal responses at both neuronal junctions and neuromuscular junctions.

All references referred to in the text are incorporated herein by reference as if fully set forth herein. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

What is claimed is:

1. An ocular implant comprising:
   (a) a housing having a surface biocompatible with at least a portion of a neuronal cell;
   (b) an aperture in said surface, wherein said surface is micropatterned for directing a neuronal cell process toward said aperture, and said aperture capable of receiving said neuronal cell process;
   (c) a reservoir containing a fluid connected to said aperture, said aperture providing a conduit for delivery of said fluid from said reservoir to said neuronal cell process in said aperture; and
   (d) a flow regulator pump in operable relationship with said fluid in said reservoir for moving said fluid to said aperture,
   wherein said implant is oxidized and coated with a polyimide layer to reduce capacitance.

2. The implant according to claim 1, wherein said flow regulator pump an electromechanical device.

3. The implant according to claim 1, wherein said flow regulator pump an electrical device.

4. The implant according to claim 1, wherein said fluid comprises a bioactive agent.

5. A method for stimulating a neuronal cell, said method comprises inserting in proximity to a neuronal site an implant according to claim 1, wherein said fluid comprises a bioactive agent.

6. The method according to claim 5, wherein said neuronal site is a retinal site.

7. The method according to claim 5, wherein said bioactive agent is a neurotransmitter.

8. An ocular implant comprising:
   (a) a housing having at least one aperture and a surface biocompatible with at least a portion of a neuronal cell, said surface being micropatterned for directing growth of a neuronal cell process to said aperture, and said aperture capable of receiving said neuronal cell process;
   (b) a reservoir containing a fluid connected by a channel to each said aperture said aperture providing a conduit for delivery of said fluid from said reservoir to said neuronal cell process in said aperture; and
   (c) an electrically controlled flow regulator pump in operable relationship with said fluid in said reservoir for moving said fluid to said apertures,
   wherein said device is oxidized and coated with a polyimide layer to reduce capacitance.

9. The implant according to claim 8, wherein said micropattern comprises bioactive agents and directs growth of said neuronal cell process to said aperture.

10. The implant according to claim 8, wherein said implant comprises at least one photodiode as the electrical source for actuating said electrically controlled flow regulator pump.

11. The implant according to claim 8, wherein said surface comprises a well, said aperture connecting said well with said reservoir via said channel.

12. An ocular implant comprising:
   (a) a housing of a flexible material having a surface biocompatible with at least a portion of a neuronal cell;
   (b) an aperture in said surface, wherein said surface is micropatterned for directing a neuronal cell process toward said aperture;
   (c) a reservoir connected to said aperture; and
   (d) a flow regulator pump operable relationship with fluid in said reservoir for moving said fluid to said aperture,
   wherein said device is oxidized and coated with a polyimide layer to reduce capacitance.

13. The implant according to claim 12, wherein said flexible material is a polysiloxane.

14. The implant according to claim 12, wherein said housing is comprised of two layers:
   (a) a first layer comprising at least one reservoir and at least one channel, each of said at least one reservoir connected to one of said at least one channel; and
   (b) a second layer covering said first layer enclosing said at least one reservoir and said at least one channel and having an aperture in communication with said at least one reservoir.

15. The implant according to claim 14, wherein said second layer is micropatterned for directing growth of a neuronal process to said aperture.

16. The implant according to claim 12, wherein said fluid comprises a bioactive agent.

17. The implant according to claim 12, wherein said flow regulator pump is an electromechanical device.

18. The implant according to claim 17, wherein said implant comprises photodiodes and said electromechanical device is actuated by photodiodes.

19. The implant according to claim 12, wherein said flow regulator pump is an electrical device.

20. The implant according to claim 19, wherein said device comprises photodiodes and said electrical device is actuated by photodiodes.

21. A method for stimulating a neuronal cell, said method comprises inserting in proximity to a neuronal site an implant according to claim 12, wherein said fluid comprises a bioactive agent.

22. An ocular implant comprising:
   (a) a housing having a surface biocompatible with at least a portion of a neuronal cell;
   (b) an aperture in said surface;
   (c) a reservoir connected to said aperture; and
   (d) a flow regulator pump in operable relationship with fluid in said reservoir for moving said fluid to said aperture, wherein said flow regulator pump comprises at least one of a flexible housing, a flexible membrane pump or a light sensitive polymer flow regulator pump;
   wherein said device is oxidized and coated with a polyimide layer to reduce capacitance.

* * * * *